United States Patent [19]

Goldsberry

[11] Patent Number: Plant 6,642

[45] Date of Patent: Feb. 28, 1989

[54] DWARF CARNATION PLANT 'SNOWMASS'

[75] Inventor: Kenneth L. Goldsberry, Fort Collins, Colo.

[73] Assignee: Colorado State University Research Foundation, Fort Collins, Colo.

[21] Appl. No.: 71,082

[22] Filed: Jul. 10, 1987

[51] Int. Cl.[4] ..... A01H 5/00

[52] U.S. Cl. ..... Plt./70

[58] Field of Search ..... Plt./70–73

*Primary Examiner*—James R. Feyrer

*Attorney, Agent, or Firm*—Edwin L. Spangler, Jr.

[57] ABSTRACT

A carnation plant known by the cultivar name Snowmass was developed through a breeding program and is particularly characterized as to uniqueness by its dwarf growth habit and the following combined characteristics: upon pinching a rooted cutting, forms 3 to 5 lateral stems 22 to 26 cm long, each developing a terminal flower and 4 to 6 lateral buds which open intermittently after the terminal flowers seneses; white flowers 4.5 to 5.5 cm in diameter, but without fragrance; can be grown under specified conditions either as a single pinched plant per 10 cm pot or 3 pinched plants per 13 cm pot, which results in an ideal new flowering house plant.

1 Drawing Sheet

My present invention relates to a new and distinct dwarf cultivar of *Dianthus caryophyllus* Linn. identified as plant 246-18 and given the name Snowmass.

Snowmass is a product of a breeding program started by me at Colorado State University in 1974, using commercially available semi dwarf germplasm, crossing selected unnamed seedlings and incorporating various known carnation germplasm with an objective of creating dwarf carnation cultivars that could be asexually produced for commercial use, in controlled environments, as flowering house plants.

Snowmass was originated from a cross made in a controlled breeding program at the Horticulture Department, W. D. Holley Plant Environmental Research Center, Colorado State University, Fort Collins, Colo. using the unnamed seed parent 83-20-14 and an unnamed pollen parent 83-12A, also developed by the present inventor.

Snowmass was discovered and selected as one flowering plant within the progeny of the stated cross by Kenneth L. Goldsberry on Aug. 30, 1985 in a controlled environment in Fort Collins, Colo.

The first act of asexual reproduction of Snowmass was accomplished when vegetative cutting's were taken, by the inventor, from the initial selection on Oct. 10, 1985 in a controlled environment in Fort Collins, Colo. The initial rooting of the cuttings and performance of the resulting plants has demonstrated that the distinctive characteristics of this new cultivar Snowmass, here in disclosed, appear to be firmly fixed and hold true from generation to generation.

Snowmass has not been observed under all possible environmental conditions. The phenotype may vary significantly with variation in the product environment including irrigation regimes, temperature, light intensity, day length and nutritional programs. It has been observed and evaluated, from a rooted cutting to a mature plant while being grown in Fort Collins and Denver, Colo. and Encintias and Salinas, Calif. under greenhouse conditions, which approximate those generally used in commercial practice.

The following traits, which have been repeatedly observed, characterize Snowmass and distinguishes it as a new and distinct dwarf carnation cultivar:

1. Somatic chromosome is 2n=30

2. A double type flower, similar to commercial cut flower spray types
3. Flower size ranges from 4.5 to 5.5 cm in diameter
4. White colored flowers
5. Medium flowering response on a scale of early, medium or late flowering
6. Three to five lateral shoots develop following a pinch of the main stem
7. The terminal flower, four to six secondary buds and two to six tertiary buds form on each lateral stem. As the terminal flowers senese, the secondary buds continue to open, the tertiaary buds usually abort
8. Peduncle length of secondary buds on a single stem varies between 1.5 to 16.5 cm
9. Plant height ranges between 19 to 23 cm
10. The flowers have no fragrance There are no dwarf carnation cultivars, for house plant use, presently developed and known to the inventor.

BRIEF DESCRIPTION OF THE DRAWING

The accompanying top colored photograph taken on July 9, 1987, using an 18 percent Kodak photographic gray card as a color base, illustrates in perspective view and the overall appearance of Snowmass (85-246-18) grown in 10 cm (single plant) and 15 cm (3 plants) azalea pots. The bottom photo shows buds, inflorescence, stem, foliage characteristics and color of Snowmass are typical and true as possible with illustrations of this type.

The following detailed description of my new dwarf carnation cultivar are based upon observations of greenhouse grown plants made in 1986 and 1987 at Fort Collins, Colo. The color values were determined in a standard color viewing booth with a 5000° K. fluorescent light source using references developed and published by The Royal Horticultural Society, London, England.

PLANT CHARACTERISTICS

Origin: Seedling selection.

Parentage:

*Seed parent.*—Selected unnamed seedling, 83-20-14 (Goldsberry).

*Pollen parent.*—Selected unnamed seedling 82-12A (Goldsberry).

Classification:

*Botanic.*—*Dianthus caryophyllus* Linn. cv. Snowmass.

*Commercial.*—Dwarf carnation for pot plant production.

Propagation: Vegetative cuttings, 6 to 8 cm. in length initiate visible roots in 8 to 10 days in the winter and 5 to 8 during the summer, when rooted under mist in a rooting medium temperature of 20° C. A quality rooted cutting with an abundance of roots, is usually ready to plant in 15 days in the summer and 18 to 20 in the winter.

Growth habit: Three to five lateral shoots form naturally, but are accelerated by removing the terminal portion of the main stem, at the sixth or seventh node from the top, resulting in a compact, bushy and strong up right plant. Some basal branches may elongate enough to place apical buds on a plane 2–5 cm above or below the terminal flowers of the initial stems.

Stems: Numerous lateral branches form close to the base of the plant and vary in length from 22–26 cm, having 6 to 8 nodes with opposite leaves. A reproductive bud usually forms at each upper 5 nodes. Shoots forming at the sixth to eighth node below the terminal flower, usually develop into another flowering stem in proper environmental conditions. All stems have a blue-grey glaucous condition, approximating 189A in color.

Foliage: Leaves are abundant and typical of the commercial carnation type. The leaves at the sixth and seventh nodes from the top of each stem range in length from 9.4 to 12.2 cm and the widest leaves occur at the fifth node and have an average width of 1.0 cm, but are progressively smaller above and below these positions. Both the upper and lower sides of the leaves are dark green and have a blue-grey glaucous condition. The color of both surfaces is identified as 189A with the surface bloom present and 139A when it is removed.

INFLORESCENCE CHARACTERISTICS

Buds: Terminal buds average 2.6 cm in length just prior to opening and the secondary buds 2.5 to 2.7 cm. The average bud circumference ranges from 4.9 cm for the terminal and secondary buds 4.6 cm at the first sign of petal color. Tertiary buds usually develop on the top three secondary stems. All buds are oval in shape and pointed. Some splitting has been noted in terminal buds.

Sequence of development: The terminal bud on each stem will show color before any secondary bud color is visible. The opening sequence at the top five secondary buds at node positions is very irregular and a pattern can not be established. In the proper environments, new flower bearing shoots emerge from the sixth to eighth nodes below the terminal flower and at the base of the plant, creating a perpetual flowering condition.

Flowering response: A plant pinched 2 to 3 weeks after planting will flower 12 to 13 weeks following the pinch from a October 1 to 13 weeks following the pinch from a October 1 plant date and 9 to 10 weeks from a June 1 date in Fort Collins, Colo. when growing temperatures approximate 11° C. at night and 17° C. during the day.

Inflorescence type: Each initial stem is a semi-compound spray with a terminal bud, 5 to 6 secondary and 1 to 4 tertiary buds and 3 to 5 lateral shoots.

Number of buds and flowers per stem: Each stem has a terminal flower that develops along with the upper most, of the 5 to 6 secondary and 1 to 4 tertiary buds; new flowering shoots usually form at the sixth to eighth nodes of each initial stem resulting in an potential average of 18 flowers per stem. A total of 87 to 145 buds and flowers can be on a single plant at one time. The tertiary buds will not develop petals in low light and may not open in home conditions.

Peduncle length: The average length of the peduncles range from 1.9 cm for the top secondary bud to 10.5 cm for the fifth bud from the top on each stem, when the terminal flower is in prime condition. The peduncle length for the tertiary buds varies from 0.2 to 4.2 cm.

Peduncle strength: Strong, holds flowers erect during all growing seasons; degree of brittleness is related to environmental conditions.

Flower:

*Size.*—Terminal flowers range in size from 5.0 to 5.5 cm in diameter and the secondaries 4.5 to 5.0 cm depending on the environment.

*Type.*—Commercial double with 35 to 52 moderately serrated petals with an average length of 4.2 cm and 2.3 cm wide in the terminal flower. The secondary flowers have 31 to 46 petals with an average length of 4.0 cm and are 2.1 cm wide. The tertiary buds do not open.

*Form.*—Sub hemispherical in longitudinal section with the petals adjacent to the calyx, slightly reflexed at maturity. Seldom splits in flowering stage.

Corolla color: General tonality at a distance of 1 meter: white 155B. Upper petal surface: White 155B with 53C pencil flecks on some petals. Lower petal surface: Same as the upper surface.

Keeping quality: In the greenhouse, individual flower remain aesthetically pleasing up to 6 days; in the home 6 to 10 days with room temperatures of 17° C. and high natural light intensity.

Fragrance: None.

Reproductive organs:

*Androecium.*—Typical carnation except has 27–43 filaments, aborted anthers and no pollen.

*Gynoecuim.*—Typical of carnation in all respects; pistil is 0.8 to 1.1 cm in length and has 3 to 4 styles and stigmas. The pistils are grooved similar to those of Sneffels. The stigmas are white at all stages of flower maturity.

Disease resistance: The plant has been found free of pathogen races currently associated with standard carnation cultivars, including the wilts and Etched Ring or Fleck viruses.

I claim:

1. A new and distinct cultivar of *Dianthus caryophyllus,* Linn, identified as 85-246-18 and known as Snowmass and substantially as herein described and illustrated.

* * * * *

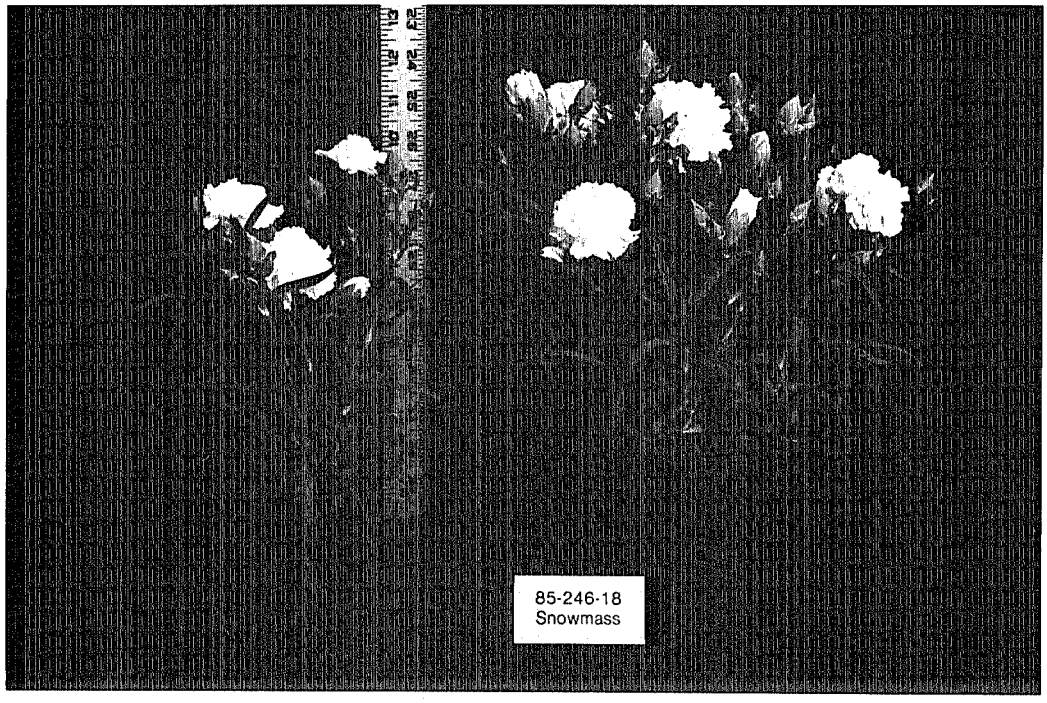
85-246-18
Snowmass
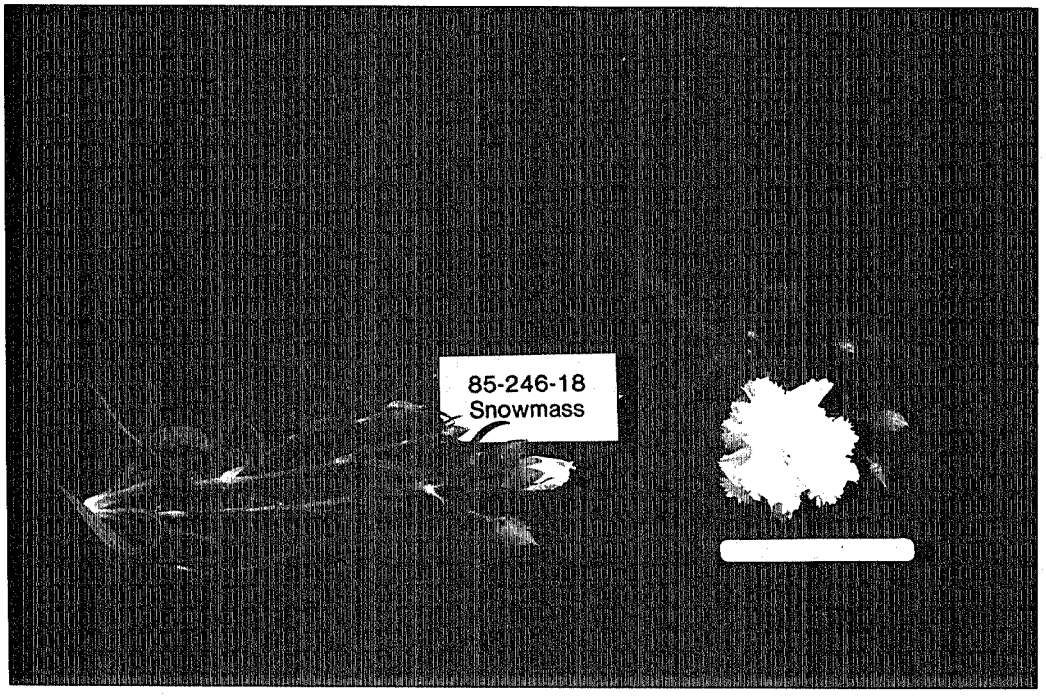
85-246-18
Snowmass